US010327799B2

(12) United States Patent
Matsuo et al.

(10) Patent No.: US 10,327,799 B2
(45) Date of Patent: Jun. 25, 2019

(54) SCISSORS

(71) Applicants: IMOTT INC., Yokohama-shi, Kanagawa (JP); Japan Organization of Occupational Health and Safety, Kawasaki-shi, Kanagawa (JP)

(72) Inventors: Makoto Matsuo, Yokohama (JP); Yoshinao Iwamoto, Yokohama (JP); Hiroshi Ujiie, Tokyo (JP)

(73) Assignee: IMOTT INC., Yokohama-Shi, Kanagawa (JP)

( * ) Notice: Subject to any disclaimer, the term of this patent is extended or adjusted under 35 U.S.C. 154(b) by 179 days.

(21) Appl. No.: 15/322,429

(22) PCT Filed: Jul. 6, 2015

(86) PCT No.: PCT/JP2015/069456
§ 371 (c)(1),
(2) Date: Dec. 27, 2016

(87) PCT Pub. No.: WO2016/051898
PCT Pub. Date: Apr. 7, 2016

(65) Prior Publication Data
US 2018/0206872 A1    Jul. 26, 2018

(30) Foreign Application Priority Data
Sep. 30, 2014 (JP) ................ 2014-202496

(51) Int. Cl.
*A61B 17/3201* (2006.01)
*B26B 13/00* (2006.01)
(Continued)

(52) U.S. Cl.
CPC .......... *A61B 17/3201* (2013.01); *B26B 13/00* (2013.01); *B26B 13/06* (2013.01);
(Continued)

(58) Field of Classification Search
CPC ...... A61B 17/3201; A61B 2017/00867; A61B 2017/00862; A61B 2017/00477;
(Continued)

(56) References Cited

U.S. PATENT DOCUMENTS 5,437,282 A * 8/1995 Koger ................. A61B 8/12
600/463
5,486,183 A * 1/1996 Middleman ........... A61B 10/02
606/113

(Continued)

FOREIGN PATENT DOCUMENTS

EP    0487645 A1    6/1992
EP    1325710 A2    7/2003
(Continued)

OTHER PUBLICATIONS

European Search Report dated Feb. 16, 2018 for European Patent Application No. 15846780.3, which is a counterpart of U.S. Appl. No. 15/322,429 (7 pages).
(Continued)

*Primary Examiner* — Ghassem Alie
(74) *Attorney, Agent, or Firm* — Lewis Roca Rothgerber Christie LLP

(57) ABSTRACT

Scissors including a pair of shanks with one end forming an upper shear blade and a lower shear blade and with the other end of the pair of shanks forming handles, the handles being opened and closed centered about a pivot where the shanks intersect and causing the upper shear blade and lower shear blade to open and close, and screw for loosely fastening the pivot with a degree of freedom so that the screws do not interfere with sliding of the blades when cutting an object, at least one of the upper shear blade and the lower shear blade being formed by an alloy having an elastic deformation ability of 0.2% or more.

8 Claims, 10 Drawing Sheets

(51) Int. Cl.
    *B26B 13/06*     (2006.01)
    *A61B 17/00*     (2006.01)

(52) U.S. Cl.
    CPC ............... *A61B 2017/00477* (2013.01); *A61B 2017/00862* (2013.01); *A61B 2017/00867* (2013.01)

(58) Field of Classification Search
    CPC ... A61B 17/2816; B26B 13/06; B26B 13/285; A61F 15/02; B25B 7/08
    USPC ... 30/254, 266, 194, 29, 196, 197, 255–260; 606/174, 206, 175; D8/57
    See application file for complete search history.

(56) References Cited

U.S. PATENT DOCUMENTS

| | | | |
|---|---|---|---|
| 5,509,923 | A | 4/1996 | Middleman et al. |
| 6,264,669 | B1* | 7/2001 | Le Louarn ............ A61B 17/24 30/254 |
| 6,592,603 | B2* | 7/2003 | Lasner ............... A61B 17/2841 30/261 |
| 2003/0120305 | A1 | 6/2003 | Jud et al. |
| 2005/0120566 | A1* | 6/2005 | Dworschak ........ A61B 17/2816 30/266 |
| 2008/0296849 | A1* | 12/2008 | Alacqua ............... F16J 15/0806 277/593 |
| 2010/0152757 | A1 | 6/2010 | Slater |
| 2012/0303049 | A1 | 11/2012 | Nakamura |
| 2015/0313618 | A1* | 11/2015 | Horikawa ............. A61B 17/30 606/210 |

FOREIGN PATENT DOCUMENTS

| | | |
|---|---|---|
| JP | 35-19539 | 8/1960 |
| JP | 53-116087 | 9/1978 |
| JP | 62-192725 U | 12/1987 |
| JP | 1989(H01)-086970 U | 6/1989 |
| JP | 04-114689 A | 4/1992 |
| JP | 04-507363 A | 12/1992 |
| JP | 05-146558 A | 6/1993 |
| JP | 2007-143956 A | 6/2007 |
| JP | 2012-090919 A | 5/2012 |
| JP | 2012-512005 A | 5/2012 |
| JP | 2012092373 A * | 5/2012 ......... A61B 17/3201 |

OTHER PUBLICATIONS

Chinese Office Action dated Mar. 5, 2019 regarding Chinese Patent Application No. 201580035803.3, which is a counterpart of U.S. Appl. No. 15/322,429 (6 pages) with English Translation (10 pages).

* cited by examiner (a)

(b)

(c)

(a)

(b)

(a)

(b)

(c)

(d)

(a)

(b)

(a)

(b)

(a)

(b)

(c)

SCISSORS

CROSS-REFERENCE TO RELATED APPLICATION(S):

This application is a National Phase Patent Application and claims the priority of International Application Number PCT/JP2015/069456, filed on Jul. 6, 2015, which claims priority of Japanese Patent Application Number 2014-202496, filed Sep. 30, 2014, the entire contents of which are incorporated herein by reference.

TECHNICAL FIELD

The present invention relates to scissors, particularly medical use scissors, and more particularly relates to scissors suitable for neurosurgical procedures etc.

BACKGROUND ART

Scissors usually are made by connecting two cutting blades through a rotatable pivot and adjusting the shear between the blades. They cut an object by placing the object between the blades and closing the blades. A structure is created enabling one contact point to reliably move from the bases to the tips to enable an object gripped between the joined parts to be cut. This system is the same both with large sizes and small sizes. The "adjustment of shear" is the work of grinding the blades by a grindstone to give the target rate of curvature at the time of honing and setting the dimensions so that the shear point "smoothly" advances to the tips by a constant force with the opposite side blade. Since it is difficult to make exactly the same blade from the way of making the two blades, so this shear adjustment work has been considered essential. This shear adjustment work has a direct impact on the cutting ability of the scissors. Paper cutting scissors and other scissors for general applications are generally made by machining, but high quality scissors, for example, medical use scissors, are often made by hand. Such scissors are given sharpness and durability by the skill of the manufacturer. For this reason, "shear adjustment" has been considered to require experience and intuition.

Hair cutting scissors have blade lengths of 50 mm to 150 mm or so. The grindstones used are also disk shaped ones of 300 mm or so in diameter. The shear adjustment work can be said to be relatively easy work since both hands are used and therefore force can be easily applied. On the other hand, medical use scissors sometimes only have blade lengths of 10 to 30 mm. There are also further smaller ones for a special use having blade lengths of only 2 mm. Therefore, manufacture currently relies on the skill of the craftsmen.

In the present circumstances, scissors have usually been made using the same grade of material for the left and right blades. They are adjusted by shear adjustment when creating bending, torsion. Usually, they are made so that the maximum performance is obtained when new. Along with use, the two blades bend and the torsion becomes off, the blades are worn down, and other abnormalities occur. To keep this to a minimum, the blades have been heat treated or made to plastically deform to try to maintain the shape.

Further, in conventional scissors, including medical use scissors, the pivot, fulcrum, and force point correspond to the screws, crescents, and blades, respectively. Blade with slight curves are screwed together to be able to rotate. The resistance received when the blade cut (resistance keeping the blades open when starting to cut) is received at the crescent, that is, the parts where the two blade slide against each other at the inner surfaces of the blades at the opposite sides to the screw. It limits movement of the blade and enables cutting. The crescents start to receive surface pressure starting from when cutting an object. As the cutting proceeds toward the tips of the blades, the pressure becomes larger, but the area corresponding to the crescents also increases.

FIG. 8 to FIG. 13 show the structures of conventional scissors. In each structure, the one ends of the pair of shanks form an upper shear blade and lower shear blade, the other ends of the pair of shanks form handles, and the handles are opened and closed around a pivot at which the shanks intersect so as to open and close the upper shear blade and the lower shear blade. The upper shear blade and the lower shear blade are generally made from the same grade of steel.

FIG. 8 shows one example of conventional medical use scissors where the tip sides are curved upward. In the figure, 11 indicates the upper shear blade, 12 the lower shear blade, 3 the pivot, 41 and 42 shanks, and 51 and 52 handles. The pair of shanks 41 and 42 cross at the pivot 3.

FIG. 9 shows the names of the parts of general scissors. In the perspective view (a), the upper shear blade is indicated by 11, the lower shear blade by 12, the fulcrum (pivot or shaft) by 3, the shanks by 41, 42, and eye rings by 43. Furthermore, cutting edges 14, bases 15, tips 16, back 17, and crescents 18 are the main elements forming the scissors. (b) is a partial view of the area around the pivot, while 19 is a pivot hole.

FIG. 10 is a schematic view of general scissors when the blades are closed and shows a lateral view. General scissors in the closed state generally strictly have a clearance between the two cutting edges of the upper shear blade and the lower shear blade.

FIG. 11 is a schematic view of the state where the blades are open in the same scissors and shows a lateral view. In the open state, strictly speaking generally the tips intersect as shown in the lateral view.

FIG. 12 schematically shows the outer surface side (a) and inner surface side (b) of one blade (11 or 12). At the outer surface side, a blade ridge is formed. At the inner surface side, crescent 18 is formed near pivot hole 19 on the shank side. The cutting edge is formed at the location where the outside surface and the inside surface of the blade intersect and has a sharpness enabling an object to be cut at a location contacting the cutting edge of the opposite side blade. Blades 11 and 12 are fastened to be able to rotate by being screwed or swaged together at pivot 3. For this reason, blades 11 and 12 are provided with pivot holes 19.

FIG. 13 shows schematic views of scissors with the tip sides curved upward used for medical use etc. (a) is a perspective view, (b) is a lateral view, and (c) is a plan view. The tip sides of the two blades are curved upward, but the structure is basically the same as normal flat blade.

SUMMARY OF INVENTION

Technical Problem

The present invention has as its object to solve the above problems and provide scissors obtained by selecting the materials sliding together, utilizing their superelasticity to enable the shapes of the blades to deform so that the blade slide against the opposite blade, and enabling cutting along the opposite blade. Further, in another preferred embodiment, the present invention has as its object to reduce the handwork of a craftsman and greatly changes the material of the blade from the conventional one and attempts to utilize the properties of the materials. That is, it has as its object the provision of scissors made of a material maintaining the hardness and sharpness required for cutting, selecting a material enabling elastic deformation along a curve of a cutting edge of an opposite member at the time of use, finished to the minimum extent as scissors, and enabling cutting even when the blade are curved upward.

Solution to Problem

The present invention provides the following invention for solving the above problem.
(1) Scissors comprised of a pair of shanks with one ends forming an upper shear blade and a lower shear blade and with the other ends of the pair of shanks forming handles, the handles being opened and closed centered about a pivot where the shanks intersect and causing the upper shear blade and the lower shear blade to open and close, at least one of the upper shear blade and the lower shear blade being formed by an alloy having an elastic deformation ability of 0.2% or more.
(2) Scissors according to the above (1) wherein the upper shear blade is formed by an alloy having an elastic deformation ability of 0.2% or more.
(3) Scissors according to the above (1) or (2) wherein the alloy has an elastic deformation ability of 1 to 7%.
(4) Scissors according to any one of the above (1) to (3) wherein the alloy is a superelastic alloy or a shape memory alloy.
(5) Scissors according to any one of the above (1) to (4) wherein the alloy is a titanium-based alloy.
(6) Scissors according to the above (5) wherein the titanium-based alloy is a β-type titanium alloy.
(7) Scissors according to any one of the above (1) to (6) wherein a tip side of the upper shear blade and the lower shear blade are curved upward.
(8) Scissors according to any one of the above (1) to (6) wherein a tip side of the lower shear blade is curved upward and a tip of the upper shear blade comprised of a superelastic alloy is rounded or made pointed for piercing.
(9) Scissors according to the above (8) wherein the upper shear blade proceeds to cut while deforming so as to follow along the upward curve of the lower shear blade.
(10) Scissors according to any one of the above (7) to (9) wherein the radius of curvature of the curve is in the range of 10 to 150 mm.
(11) Scissors according to the above (10) wherein the radius of curvature of the curve is in the range of 20 to 100 mm.
(12) Scissors according to any one of the above (1) to (11) wherein heads of a screw fastening the pivot are enlarged to broadly form surfaces sliding with the outer sides of blade parts of the scissors and the blade parts are made to move along the surfaces so that the shear blades constantly slide against each other.
(13) Scissors according to any one of the above (1) to (11) which utilizes the superelasticity of the blades to make the blades slide against each other if changing the rates of curvature of the upper shear blade and the lower shear blade and has a loosely fastened structure having a degree of freedom so that the screw does not interfere with sliding of the shear blades when cutting an object.
(14) Scissors according to any one of the above (1) to (13) for neurosurgical procedures, cardiovascular surgery procedures, plastic surgery procedures, or otorhinolaryngologic surgical procedures.
(15) Scissors comprised of a lower shear blade with an end having an upward curve and an upper shear blade with a groove cut into its shear blade, changed in thickness and worked for controlling the tensile strength, hardness, and Young's modulus of the material so as to raise the elastic deformation performance (ease of bending) of the upper shear blade, and having the upper shear blade deforming to follow along the upward curve of the lower shear blade while cutting.
(16) Scissors according to the above (15) wherein the radius of curvature of the curve is in the range of 10 to 150 mm.
(17) Scissors according to the above (16) wherein the radius of curvature of the curve is in the range of 20 to 100 mm.
(18) Scissors according to any one of the above (15) to (17) which have a structure wherein a head of a screw fastening the pivot are enlarged to broadly form surfaces sliding with the outer sides of blade parts of the scissors and the blade parts are made to move along the surfaces so that the shear blades constantly slide against each other.
(19) Scissors according to any one of the above (15) to (18) which utilize the superelasticity of the blades to make the shear blades slide against each other if changing the rates of curvature of the upper shear blade and the lower shear blade and has a loosely fastened structure having a degree of freedom so that the screw does not interfere with sliding of the shear blades when cutting an object.
(20) Scissors according to any one of the above (15) to (19) are for neurosurgical procedures, cardiovascular surgery procedures, plastic surgery procedures, or otorhinolaryngologic surgical procedures.

Advantageous Effects of Invention

According to the present invention, it is possible to provide scissors obtained by selecting materials of shear blades sliding against each other, utilizing superelasticity to enable the shape of a blade to deform so that a cutting edge slides against a curved surface of an opposite cutting edge, and therefore having blades "able to move to the point while reliably creating a single point of a cut part" along the opposite blade. According to the present invention, the shear adjustment work can be greatly reduced.

DESCRIPTION OF EMBODIMENTS

Figure 1:
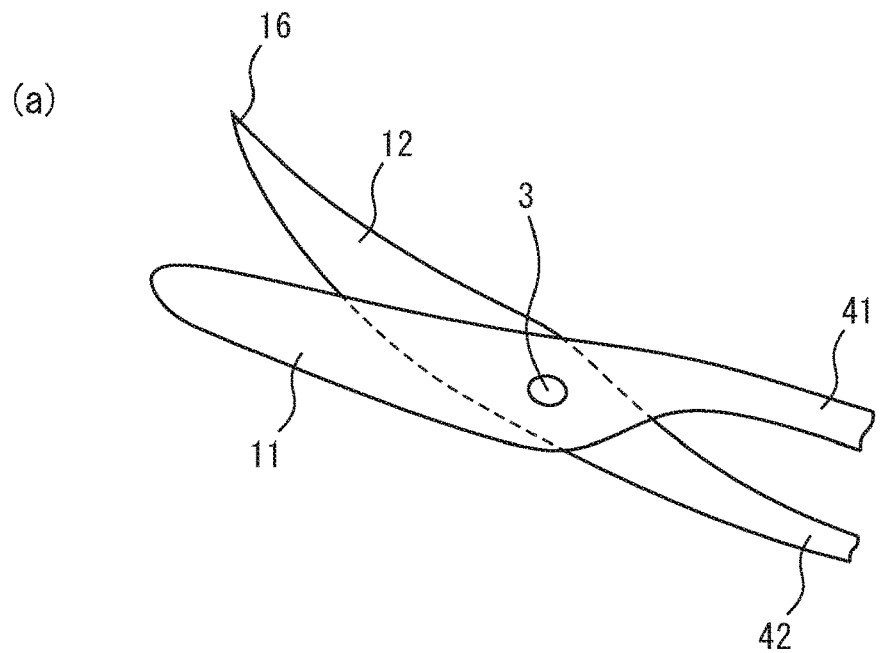
FIG. 1 is a view of scissors of one embodiment of the present invention obtained by using cutting steel for the lower shear blade and having a flat blade of a superelastic alloy for the upper shear blade.
Figure 1:
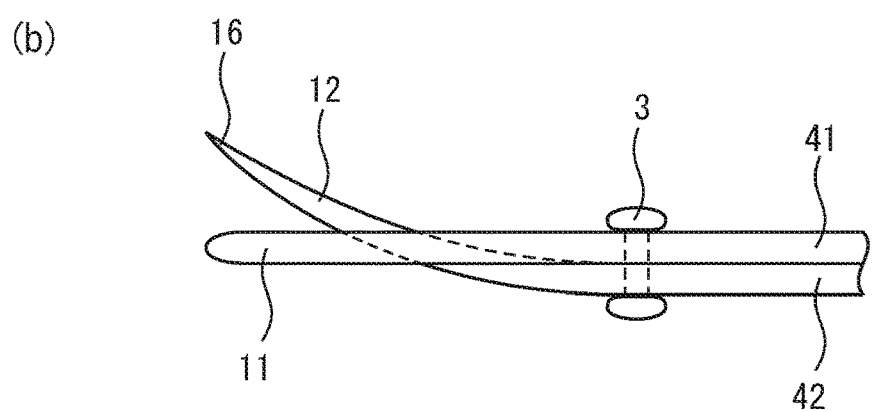
Figure 1:
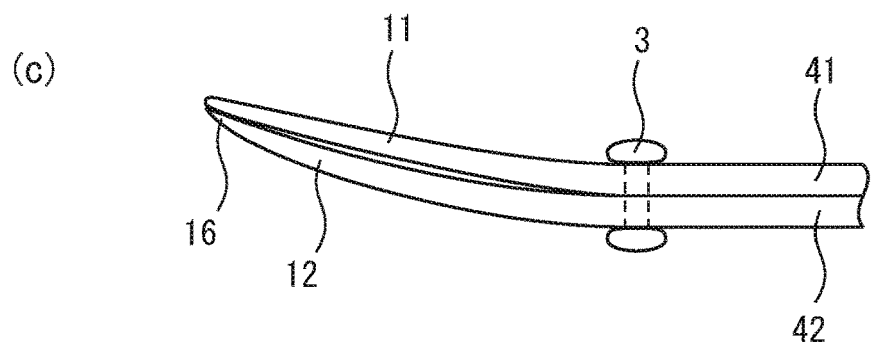

The scissors of the present invention is comprised of a pair of shanks with one ends forming an upper shear blade and a lower shear blade and with the other ends of the pair of shanks forming handles, the handles being opened and closed centered about a pivot where the shanks intersect and causing the upper shear blade and the lower shear blade to open and close, at least one of the upper shear blade and the lower shear blade being formed by an alloy having an elastic deformation ability of 0.2% or more.

The scissors of the present invention are suitably used for hair cutting and for medical use, in particular for surgery, particularly preferably for cutting tissue and other medical applications in neurosurgical procedures, cardiovascular surgery procedures, plastic surgery procedures, and otorhinolaryngologic surgical procedures.

The scissors of the present invention have at least one of the upper shear blade and the lower shear blade formed by alloy having an elastic deformation ability of 0.2% or more. Preferably, at least the upper shear blade is formed by an alloy having an elastic deformation ability of 0.2% or more. One blade of the scissors can be made using a conventional cutting steel material. A cutting steel material is mainly a stainless steel-based cutting steel or material containing nickel (Ni), chrome (Cr), and iron (Fe) as main ingredients, containing carbon (C), and being heat treated to bring out hardness. To create scissors, both hardness and toughness have to be obtained. The cutting edges can be polished down to R 1 µm or less to make them sharp. Blades are given hardness and sharpness and toughness giving resistance to breakage in accordance with the purpose of use. In some scissors, materials containing large amounts of nickel (Ni), classified as heat resistant steel by the JIS, are used. The resistance to breakage (toughness) is more emphasized rather than hardness. Resistance to breakage of the blade is sought. In particular, this is seen in use in neurosurgical procedures.

In one embodiment of the present invention, the upper shear blade is formed by an alloy having an elastic deformation ability of 0.2% or more. On the other hand, the lower shear blade is formed by a material resistant to deformation such as a high strength titanium alloy having a tensile strength of 500 N/mm$^2$ or more and a hardness of Hv240 or more. Due to this, there is little deformation of the lower shear blade. The lower shear blade receives the force that the upper shear blade pushes whereby a contact point of the blades is created by a strong pressure. If compared with the case where the lower shear blade and the upper shear blade have the same strength or elasticity, if placing the cut part at the lower shear blade side, that location is cut, so it becomes easy for the user to confirm the cut location and cut the location aimed at.

As such high strength titanium alloy, preferably β-type titanium alloy such as Ti-4Al-23V (JIS Type 80), α+β-type titanium alloy such as Ti-6Al-4V (JIS Type 60) and Ti-3Al-2.5V (JIS Type 61), and α-type titanium alloy such as Ti-5Al-2.5Sn may be mentioned.

Further, in one embodiment of the present invention, the scissors of the present invention preferably have at least one of the upper shear blade and the lower shear blade formed by a shape memory alloy. A titanium alloy such as a Ti—Ni-based shape memory alloy or Ti-36Nb-2Ta-3Zr-O (mol %) is preferable. In this case, the material should be one achieving both hardness and resistance to breakage (resistance to cracking).

The alloy used in the present invention preferably has an elastic deformation ability of 1 to 7%. More preferably, the alloy has an elastic deformation ability of 2 to 7%. Such an alloy is a titanium-based alloy having superelasticity such as a Ti—Nb-based, Ti—Mo-based, Ti—Ta-based, or Ti—Cr-based alloy or other β-type titanium alloy exhibiting superelasticity. Furthermore, a β-type titanium alloy comprised of an alloy expressed by [Ti$_{3+}$(Nb, Ta, V)+(Zr, Hf)+O (mol %)] and having a body-centered cubic structure may also be used. One having a composition of [Ti-23Nb-2Zr-0.7Ta—O (mol %)], [Ti-12Ta-9Nb-3V-6Zr—O (mol %)] or [Ti-36Nb-2Ta-3Zr—O (mol %)], etc. may be mentioned. In a superelastic alloy, even if greatly deformed by application of a deformation strain in a range not exceeding the elastic region, if removing the external stress, the deformation strain disappears and the original shape is returned to, but with a Ti—Nb-based, Ti—Mo-based, Ti—Ta-based, or Ti—Cr-based alloy or other β-type titanium alloy exhibiting superelasticity, even if applying a deformation strain of several % to 7% or so greatly exceeding the elastic limit, sometimes the change in crystal structure causes pseudo elastic deformation resulting in the original shape being returned to. On the other hand, in a shape memory alloy, if applying a deformation strain exceeding the elastic region at the transformation temperature or less, the material deforms, but if heating it to the transformation temperature or more, the deformation strain disappears and the original shape is returned to. Some shape memory alloys do not exhibit superelasticity at ordinary temperature.

Furthermore, a Ti—Ni alloy may also be suitably used. A shape memory alloy has the property of immediately returning to its original shape at the temperature of the transformation point or more even if deformed. This range of deformation is far broader compared with a usual spring etc. using steel etc. This alloy is generally an alloy of titanium and nickel, but a β-type titanium alloy of Ti-36Nb-2Ta-3Zr—O (mol %) also has a shape memory ability. When changing the composition, the property of changing to a preset shape when reaching any desired temperature or more (martensite transformation) is expressed.

In the scissors of the present invention, by making the screw used for the pivot, the shanks, and/or handles as well as the blades using a superelastic alloy, shape memory alloy, etc. it is possible to provide scissors suitable for use in the location where a nonmagnetic material is demanded.

The scissors of the present invention may be configured so that the tip sides of the upper shear blade and the lower shear blade curve upward. This is suitable for use when cutting a particularly fine part and it is necessary to facilitate viewing of the tip. This is used for the case where the user cuts while viewing the conditions around the cutting edges.

In particular, in neurosurgical procedures and cardiovascular surgery, surgery is performed by the surgeon cutting by scissors while viewing information from a microscope enlarging the operated part from above. The scissors used in this case are required to "have a blade length of 10 to 30 mm or so", "have blade parts curved (bent) so that the operated part can be seen (so as not to interfere with the field of vision of the microscope)", "have tips rounded so as not to be piercing or pointed so as to enable piercing for starting cutting", "have a high sharpness", etc. If expressing the extent of curvature by the radius R, the shear blades are curved by R 10 mm to 150 mm, preferably R 20 mm to 100 mm. If observing a blade part of a length of 15 to 30 mm under a microscope, the scissors sometimes appear in about ⅓ to ½ of the image (monitor image), so narrow width scissors are preferred. The surgeon and patient view the same image, so a structure where just the tips and cutting part of the scissors enter the field of vision is preferable. The scissors may be configured so that the tip side of the lower shear blade has an upward curve and the tip of the upper shear blade comprised of the superelastic alloy is rounded or made pointed to enable piercing. In this case, the blade part of the upper shear blade can cut while deforming so as to follow along the upward curve of the lower shear blade.

The screw for fastening the pivot may be structured broadly forming the surfaces sliding against the outsides of the blade parts of the scissors and enabling the shear blades to constantly slide against each other by the blade parts moving along those surfaces.

Further, it is possible to utilize the superelasticity of the blades to have the cutting edges slide against each other if changing the rates of curvature of the upper shear blade and the lower shear blade and to obtain a structure where the shear blades constantly slide against each other as the structure for loose fastening having a degree of freedom so that screw does not interfere with sliding of the shear blades when cutting an object.

If storing the required shape or giving a curved shape in one shear blade, the other shear blade need not be flat. For example, it is possible to make the shape memory alloy deform at the deformation temperature or less in accordance with need, store that shape, and use that for sliding of the shear blades. In this case, by a scissors employing a shape memory alloy for the upper shear blade, storing a shape of the rate of curvature R1 in advance, and using a superelastic alloy curved by a rate of curvature smaller than the upper shear blade for the lower shear blade, it is possible to use the upper shear blade to identify the cutting point and use the lower shear blade to cut there. The user can view a cutting location and cut extremely close to it.

Even without "fabricating two blades strictly adjusted for shearing and creating a structure where the two shear blades constantly slide against each other" as sought for conventional scissors, in the scissors of the present invention, the blade rotate around the screw whereby a shear blade deforms so as to approach and follow the shear blade of the opposite side, so there is no need to fabricate high precision parts integral with the shear blades, including the crescents, which has been required in conventional scissors. In the scissors of the present invention, the crescent becomes merely a contact surface.

According to one embodiment of the present invention, the pliable blade made of the superelastic alloy cuts an object while deforming so as to follow along the shear blade having an R made by the cutting steel. When the superelastic alloy is thin, it easily deforms. Even with a rate of curvature R of 20 mm, in a blade of a length 30 mm, the necessary part can deform and bend. Further, since it has a high tensile strength, it will not easily break (crack). In superelastic alloys, in Ti-23Nb-2Zr-0.7Ta—O (mol %), Ti-12Ta-9Nb-3V-6Zr—O (mol %), and Ti-36Nb-2Ta-3Zr—O (mol %), the hardness of the former has a Vicker's hardness Hv of 240 or more. This is low compared with the hardness Hv of an iron-chrome-based cutting steel of Hv550 to 630 or so. However, compared with the hardness Hv of SUS301-CSP-H of 300 to 450 etc., the hardness is a little lower in extent. There are iron-based spring steel SK5 with a hardness HRC59 after thermal refining (675 converted to Hv) and materials with a hardness HRC58 to 62 (Hv650 to 750) sold as actual cutting steel, but to create the required R (R20 to 100 mm) with such materials, it is necessary to grind or cut the material before heat treatment to create the rough dimensions then thermally refine the material (quench and temper) and polish the material to finish it to the target rate of curvature R (mm). After temper refining, bending by R 20 to 100 mm is impossible. The reason is that the material ends up breaking if the toughness is smaller than the deformation stress. The sharp cutting edges of the blades end up breaking. (A material breaks when its elongation ability (deformation ability) is smaller than the lateral deformation stress (bending). In general, cutting steel or other high hardness material has a small deformation ability.

Among superelastic alloys, the one shown by $Ti_3$(Nb, Zr, V)+(Ta, Hf)+O has a particularly excellent toughness and hardness and will not break even if bent 180 degrees. Further, as Ti-based alloys exhibiting an elastic deformation ability of several % to 7%, there are a Ti—Nb-based, Ti—Mo-based, Ti—Ta-based, and Ti—Cr-based alloy. It is sufficient to selectively use materials suitable for the purpose of the scissors which will not break. Having broken pieces of scissors remaining in the operated part in neurosurgical procedures is extremely dangerous. It is necessary to absolutely ensure that scissors do not break at the operated part.

When giving the scissor blade a coating with a high hardness, in particular when forming a film by CVD, the Ti alloy can be coated without an intermediate layer of Ti, Si, Cr, etc. and the adhesion between CVD coating material and base material of Ti is good.

In hair cutting scissors, ones coated with a finely divided diamond-like carbon film at the inside surfaces of the blades are provided, and there are reports that due to the effect of the hard film having the low coefficient of friction, the wear of the cutting edges is reduced and the sharpness can be maintained longer. In the present invention as well, by coating the upper shear blade and the lower shear blade with a finely divided diamond-like carbon film, the abrasion between the two blades can be reduced and the resistance at the time of cutting can be decreased. Further, the wear resistance of the blades is improved and the lifetime can be made longer.

In the scissors of the present invention as well, the resistance at the time of cutting starts to be applied to the crescent parts through the screw, but even if the crescent parts become worn, the shear blades elastically deform so that the blade approaches the opposite blade, so it is possible to enable cutting along the opposite blade over the deformation of the crescent parts due to wear and the scissors can be reconditioned for recovering the performance by the screw adjustment.

In one embodiment of the present invention, the scissors is configured comprised of a lower shear blade with a tip side having an upward curve and an upper shear blade with a groove cut into its shear blade, changed in thickness and worked for controlling the tensile strength, hardness, and Young's modulus of the material so as to raise the elastic deformation performance (ease of bending) of the upper shear blade, and having an upper shear blade deforming to follow the upward curve of the lower shear blade while cutting. The purpose of forming a groove in the upper shear blade other than the cutting edge is to utilize the fact that the groove becomes relatively thinner compared with the surrounding material and deformation becomes easier at the groove part and take advantage of the "control of bending" and the "ability to limit the positions of bending". The groove may be a single groove or multiple grooves. The directions, widths, depths, and lengths can be freely determined. For the groove shapes, U-shapes, V-shapes, square-shapes, R-shapes, barrel-shapes, and combinations of these may be employed. Due to this, it becomes possible to precisely create the optimal strength of the blades for cutting and the ability for elastic deformation along the opposite blade. This groove may also be provided at either the sliding surface and outside surface of the blade. Further, the forming of the grooves on the blades can be done partially or fully on the blades.

As the method of forming the groove, laser processing, cutting, grinding, plastic forming, etching, EB (electron beam) processing and other methods using electrons, and photolithography plus etching may be employed.

Further, the change of thickness is different from the change of thickness of material used for conventional scissors (a change that uniformly becomes thinner from base toward tip). It is a change of thickness facilitating elastic deformation at a location which a designer designates for bending or curving. To change the thickness, flattening by cold working or cutaway by cutting or grinding can be employed. As the method of changing the hardness and Young's modulus, one of a cold wrought operation or cold forging, heating and rapid cooling, heating and slow cooling, and annealing or a combination of the same can be performed for changing the tensile strength, hardness, and Young's modulus of the material in accordance with the purpose.

Below, the structure of the scissors of the present invention will be explained in further detail for embodiments of the present invention regarding the drawings. FIG. 1 is a view schematically showing the main parts for explaining the structure and feature of scissors of the present invention in an easily understandable manner. FIG. 1 shows an example where upper shear blade 11 is formed of a superelastic alloy, for example, is formed of an alloy expressed by $Ti_3(Nb, Ta, V)+(Zr, Hf)+O$. Lower shear blade 12 is formed by a stainless steel-based cutting steel. Furthermore, in another embodiment, lower shear blade 12 is also formed by a superelastic alloy or shape memory alloy.

The situation is the same even when using a Ti—Ni-based shape memory alloy or a shape memory alloy expressed by Ti-36Nb-2Ta-3Zr—O (mol %) for the lower shear blade. The Ti—Ni-based shape memory alloy or Ti-36Nb-2Ta-3Zr—O (mol %) shape memory alloy of the lower shear blade in this case has a high hardness relative to the upper shear blade and also becomes smaller in elastic deformation ability. These shape memory alloys are materials resistant to cracking as compared to cutting steel, so is suitable for use in locations where fracture would be a problem.

In the aspect of the present invention shown in FIG. 1, the tip (point) 16 of lower shear blade 12 has an upward curve. Therefore, this is used in the case where, when cutting a particularly fine part, the user can cut while viewing the situation around the tip. In particular, in neurosurgical procedures, this is suitable when a surgeon performs surgery while viewing information from a microscope enlarging the operated part from above. The tip is preferably rounded so as not to pierce an operated part when it should not be pierced and conversely is preferably made pointed when piercing the operated part. If showing the extent of curvature of the curve by the radius R, curvature by an R of 20 mm to 100 mm is preferable. In FIG. 1, (a) is a perspective view, (b) is a view showing the lateral view in the state with the blades opened, and (c) is a view showing the lateral view in the state with the blades closed. The tip side of lower shear blade 12 is curved upward. Upper shear blade 11 is a flat blade. When closing the blade, the large elastic deformation ability of shear blade 11 causes it to follow along lower shear blade 12. The blades contact each other at one point of cutting edge 14. The point where they contact moves toward tip 16 along with the operation for closing the blades. The object is cut at the contact point.

Pivot 3 forms broad surfaces at the fastening screw sliding against the outer sides of the blade parts of the scissors. A structure where the blade parts move along these surfaces whereby the shear blades constantly slide against each other is preferable.

Figure 2:
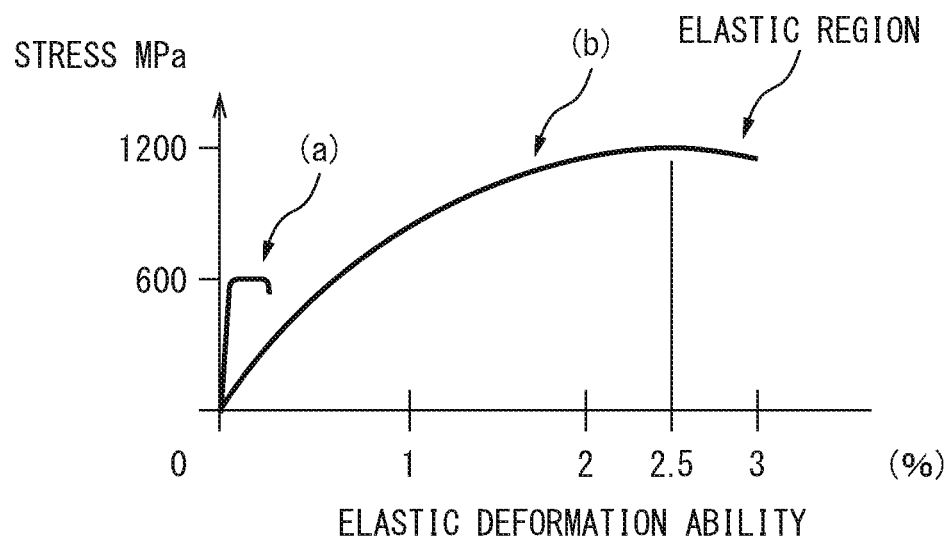
FIG. 2 is a view schematically showing the characteristics of elastic deformation ability (strain)/stress of a superelastic alloy and a general steel material.

FIG. 2 is a view schematically showing the characteristics of the deformation ability (strain)/stress of a superelastic alloy and general steel material and shows a comparison of the general characteristics of deformation ability vs. stress of a superelastic alloy with the general characteristics of the deformation ability vs. stress of general steel. (a) shows the elastic deformation ability of a ferrous metal-based scissor steel (<0.2), while (b) shows the nonlinear elastic deformation ability up to 2.5% of a superelastic alloy such as $Ti_3(Nb, Ta, V)+(Zr, Hf)+O$. It is shown that the elastic deformation ability of a superelastic alloy is extremely large compared with general steel.

Figure 3:
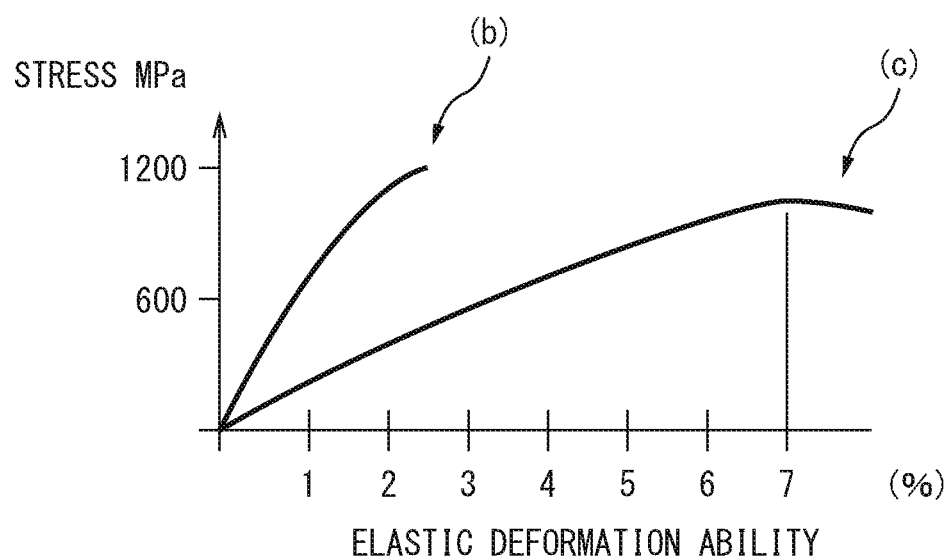
FIG. 3 is a view schematically showing the characteristics of the typical deformation ability (strain)/stress of a superelastic alloy and the characteristics of the deformation ability (strain)/stress of a superelastic alloy showing the superelasticity up to 7% including pseudo elastic deformation ability.

FIG. 3 is a view schematically showing the characteristics of the typical deformation ability (strain)/stress (b) of a superelastic alloy expressed by $Ti_3(Nb, Ta, V)+(Zr, Hf)+O$ (mol %) and the deformation ability (strain)/stress (c) of a superelastic alloy exhibiting superelasticity up to 7% including pseudo elastic deformation in Ti—Nb-based, Ti—Mo-based, Ti—Ta-based, and Ti—Cr-based alloys. It shows in comparison graphs of the elastic deformation ability/stress of a material of an alloy having an elastic deformation ability of 2.5% such as $Ti_3(Nb, Ta, V)+(Zr, Hf)+O$ and a material having an elastic deformation ability of 7% including the pseudo elastic deformation in a Ti—Nb-based, Ti—Mo-based, Ti—Ta-based, and Ti—Cr-based alloy. Each has an elastic range exhibiting a nonlinear elasticity.

The above FIG. 1 shows one embodiment of the scissors of the present invention and is the case where the lower shear blade is made using a general cutting steel and the other upper shear blade is formed of a superelastic alloy. In particular, the tip side of the lower shear blade is bent upward (worked so that the shear blade has concave shape). The biggest feature is exhibited when configuring the upper shear blade by flat plate. That is, if closing the two blades of the scissors so as to cut an object, the upper shear blade with the large deformation ability moves while deforming so as to follow along the upward curve of the rigid lower shear blade so as to cut the object.

Figure 4:
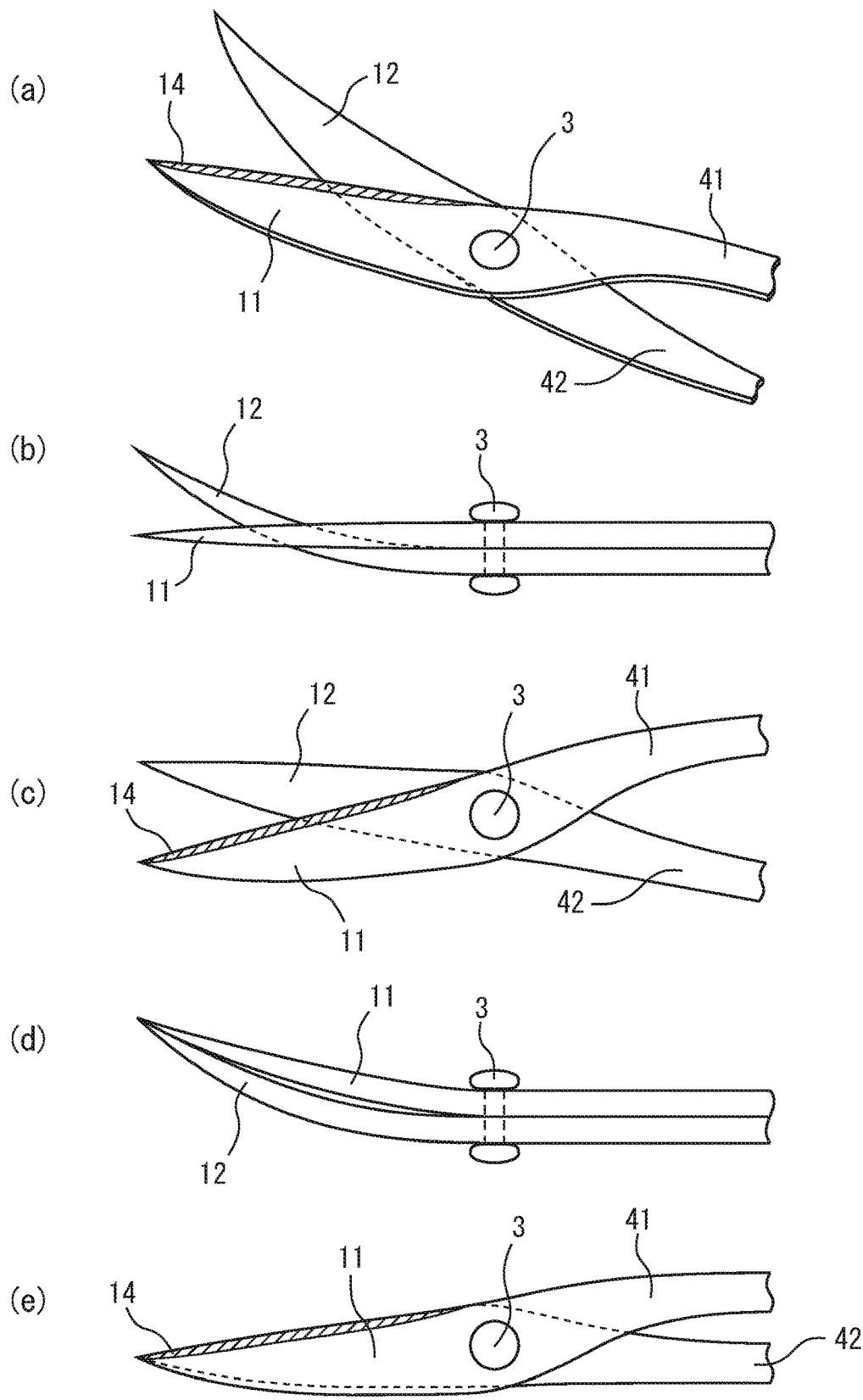
FIG. 4 is a view showing one embodiment of the present invention.

In FIG. 4, (a) shows a perspective view, (b) and (d) show lateral views, and (c) and (e) show plan views respectively simulating such an operation. (b) is a lateral view of the state where the two blades are open, while (C) is a plan view of the state where the two blades are open. (d) is a lateral view of the state where the two blades are closed, while (e) is a plan view of the state where the two blades are closed. In the same way as FIG. 1, in FIG. 3 as well, if explaining the operation of the blades, upper shear blade 11 deforms along lower shear blade 12 while cutting as upper shear blade (11) and lower shear blade 12 close.

As another embodiment of the present invention, it is possible to improve the "ease of deformation" of the blades by additionally working the blades. For example, by using the above-mentioned material having an elastic deformation ability of 0.2% to the blades, the example may be considered of using additional working to more greatly raise the "ease of deformation".

Figure 5:
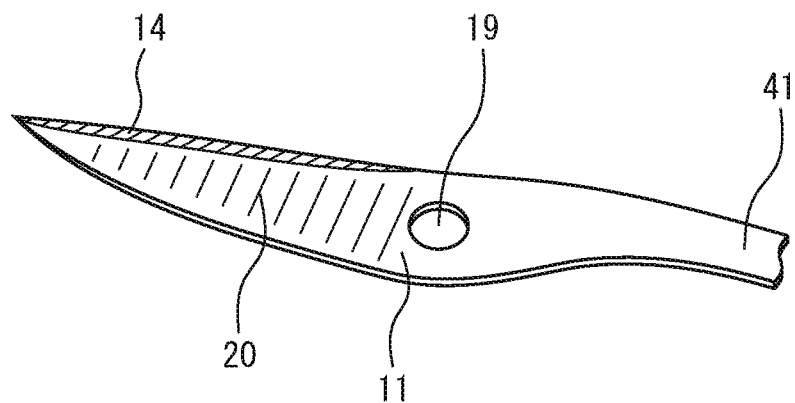
FIG. 5 is a view showing one embodiment of the present invention of a worked state adding grooves to a blade for improving the elastic deformation performance of the blade.
Figure 5:
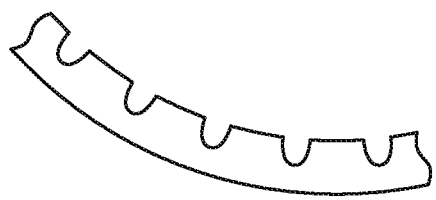
Figure 5:

In FIG. 5, (a) shows an example where grooves 20 are formed in a part of upper shear blade 11 other than cutting edge 14. As the method of forming the grooves, one may be selected from laser processing, cutting, grinding, plastic forming, etching, EB processing and other methods using electrons, and photolithography plus etching or a combination of these may be employed. (b) schematically shows a curved state of a blade. The curve may be given to either the inside surface side and outside surface side. (c) shows an example of the cross-sectional shapes of the grooves. For the groove shapes, U-shapes, V-shapes, R-shapes, barrel-shapes, square-shapes, and combinations of these may be employed. The groove widths, depths, positions, directions, numbers, lengths, whether the grooves are formed in parallel or not in parallel or whether they intersect, and other conditions may be selected or combined from the ease of bending or the effects of the grooves. The grooves of (c) may be provided on either the outer surface sides of the shear blade or on the sliding inner surface sides or on both sides. The working processes of (a) to (c) are not shown in the drawings, but it is possible to provide the grooves at the blade of the upper shear blade and the lower shear blade other than the cutting edges.

Figure 6:
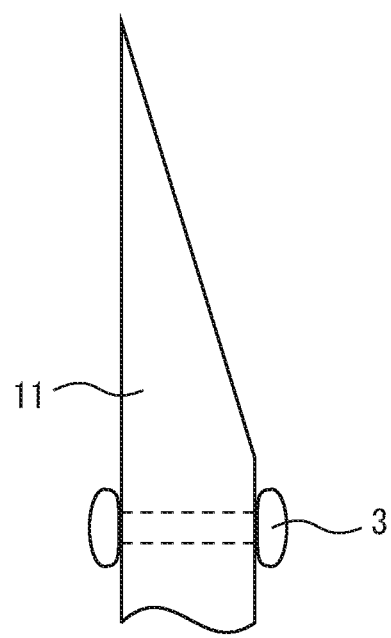
FIG. 6 is a view showing one embodiment of a worked state changing in stages the thickness of blades in the longitudinal direction so as to improve the elastic deformation performance of the blades.
Figure 6:
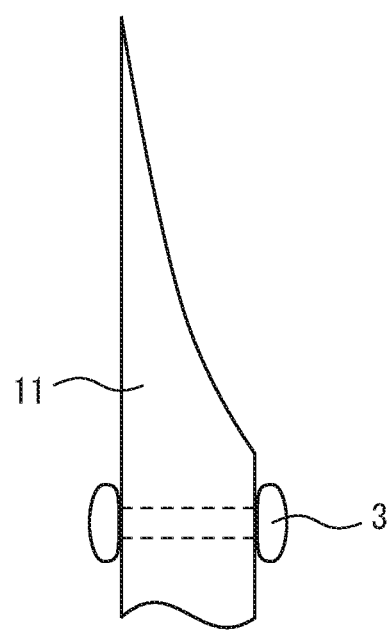

FIG. 6 shows examples of gradually changing the thickness of the upper shear blade. (a) shows an example of linearly changing the thickness, while (b) shows an example of changing to a recessed shape by any shape. If the values of the physical properties of the materials are the same, the mode of the bending changes proportionally to the thickness. This change in mode of bending can be obtained by changing the thickness. There is no need to change the thickness uniformly. It is possible to utilize a change of thickness corresponding to the objective. It is also possible to fabricate a blade part having a cutting edge having the target strength by working it. Accurate cutting therefore becomes possible.

Figure 7:
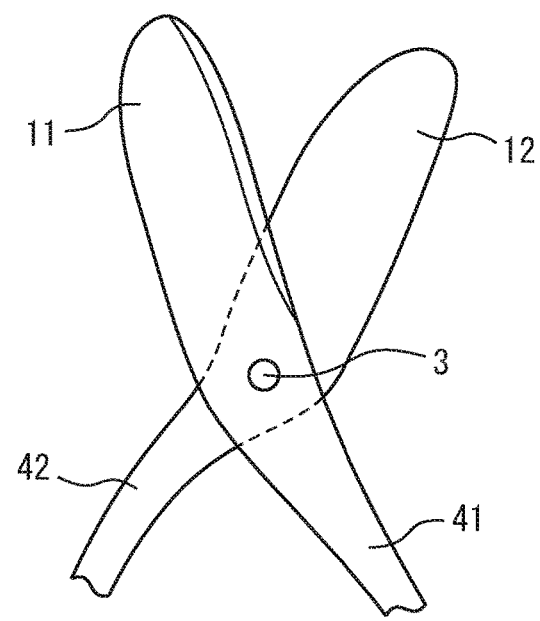
FIG. 7 is a schematic view showing the state of opening and closing of scissors obtained by preparing both a lower shear blade and the upper shear blade by a superelastic alloy and combining them.
Figure 7:
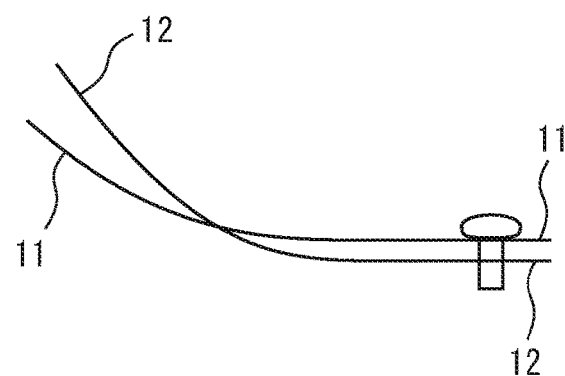
Figure 7:
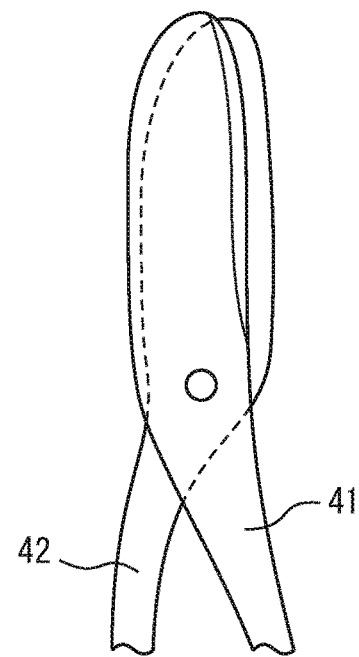
Figure 7:
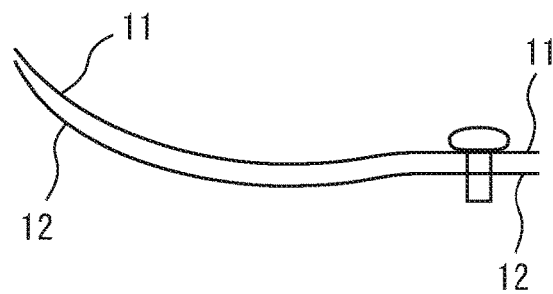
Figure 8:
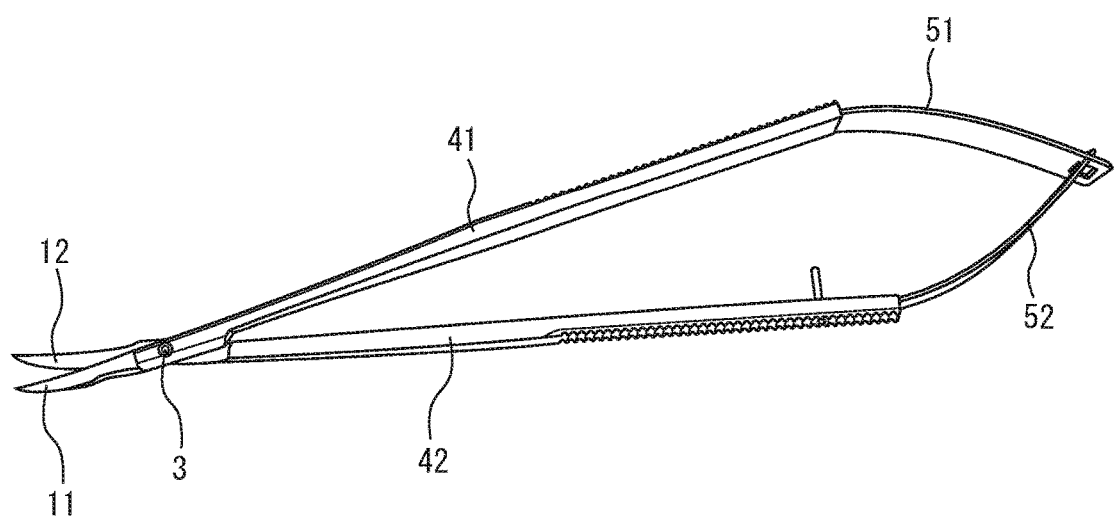
FIG. 8 is a view showing one example of conventional medical use scissors.
Figure 9:
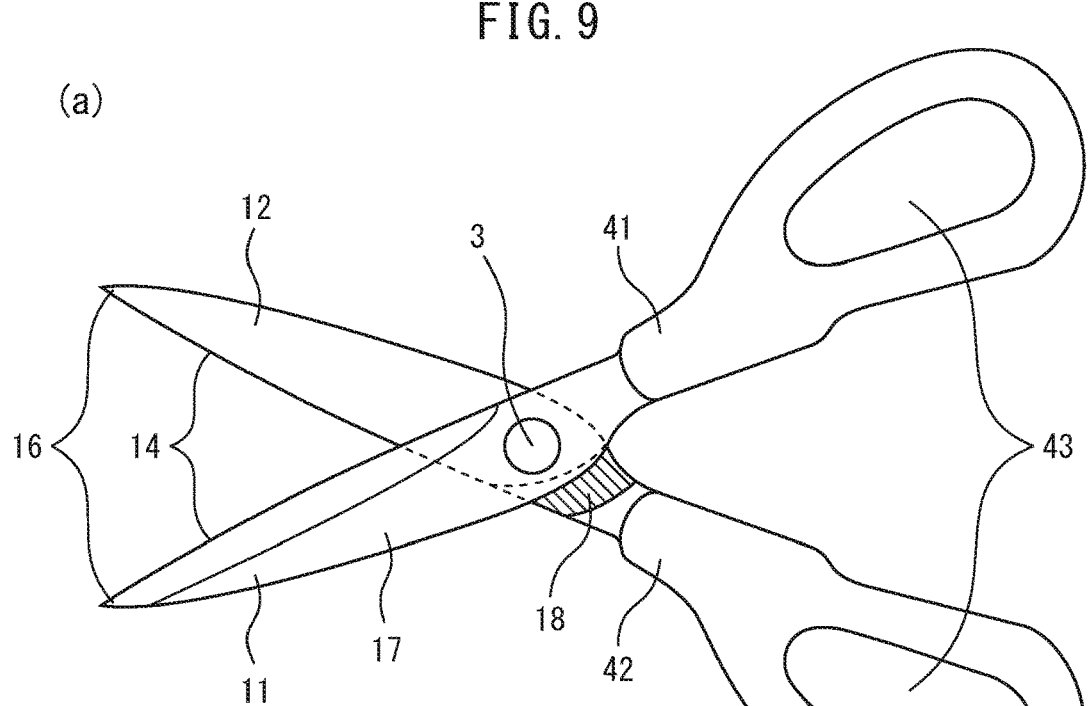
FIG. 9 is a view showing names of the parts of scissors.
Figure 9:
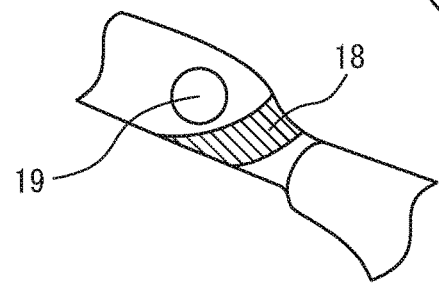
Figure 10:
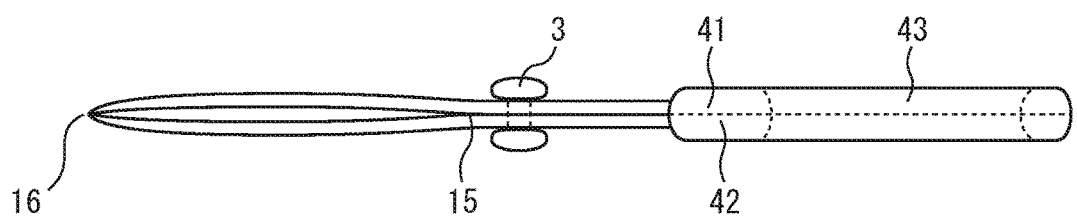
FIG. 10 is a lateral view showing a closed state of conventional scissors.
Figure 11:
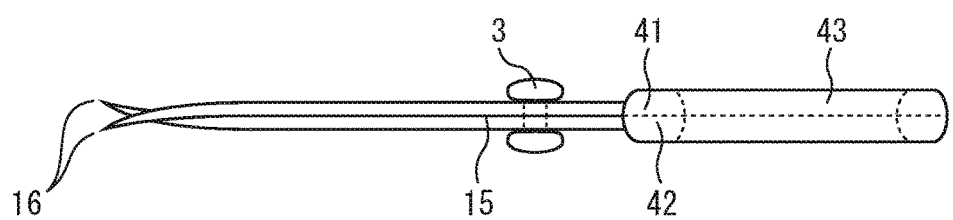
FIG. 11 is a lateral view showing an open state of conventional scissors.
Figure 12:
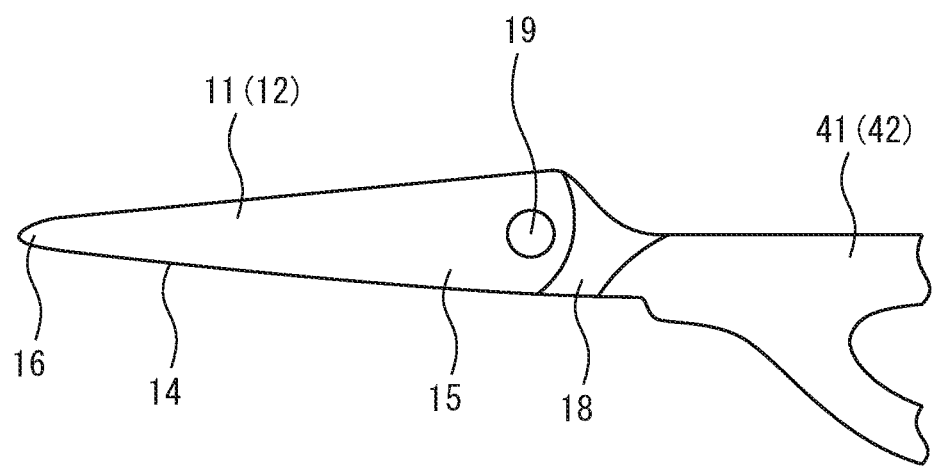
FIG. 12 is an enlarged view of the blades of conventional scissors.
Figure 12:
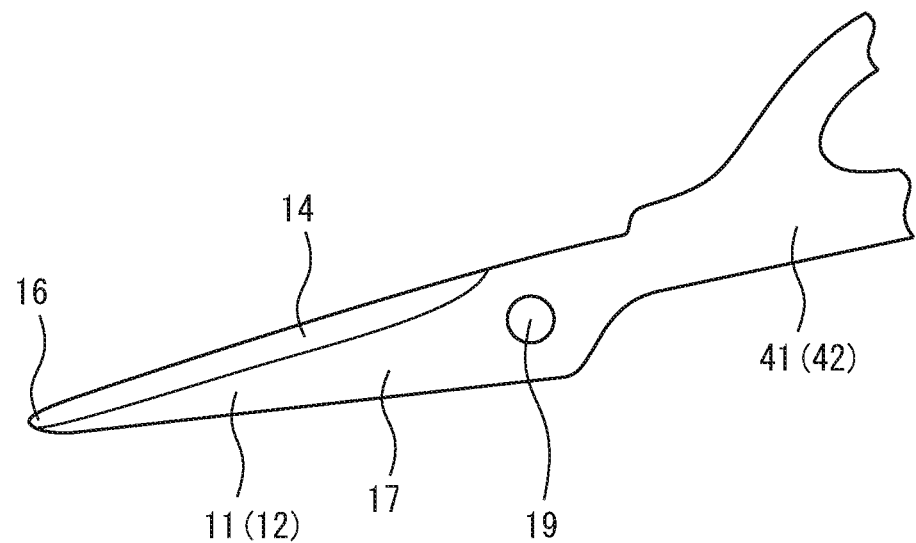
Figure 13:
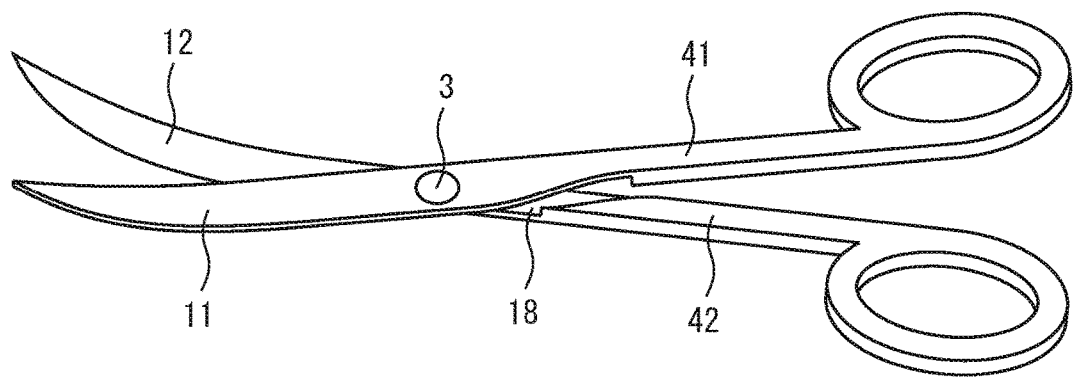
FIG. 13 is a view showing one example of conventional medical use scissors.
Figure 13:
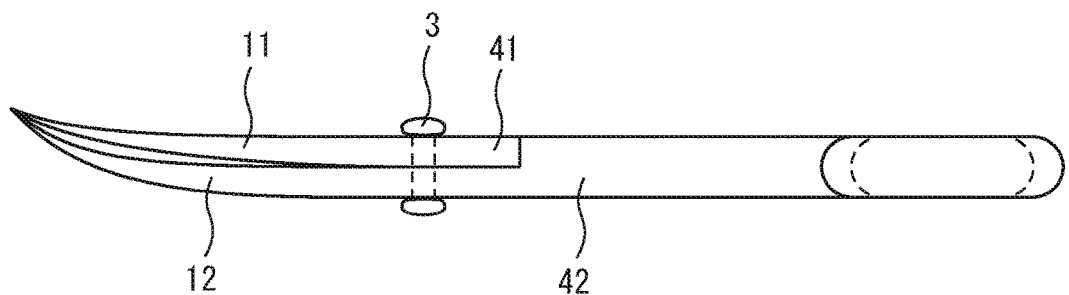
Figure 13:
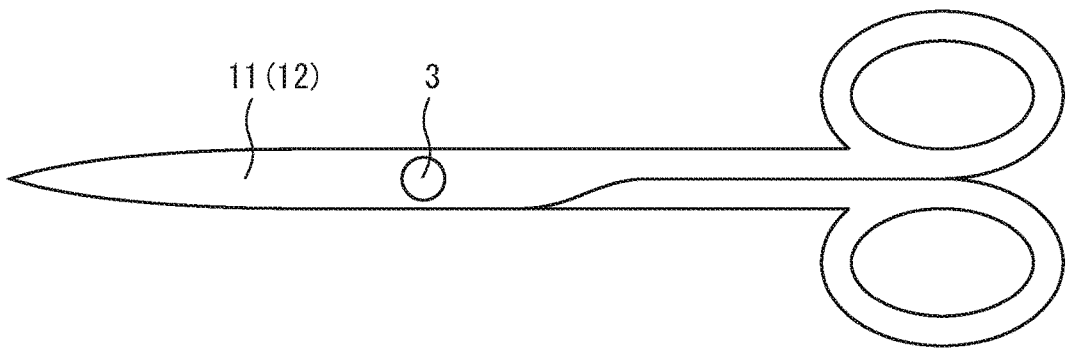

FIG. 7 is a view of a combination of blades using a superelastic alloy for the upper shear blade and the lower shear blade and given different rates of curvature for both, wherein (a) is a plan view at the time of opening the scissors, (b) is a side view at the time of opening (lateral view), (c) is a plan view at the time of closing the scissors, and (d) is a side view at the time of closing (lateral view). Here, when closing both blades, the upper shear blade is pressed to curve upward while the lower shear blade is pressed to deform to a stretched shape. That is, the lower shear blade is formed to be strongly bent while the upper shear blade is formed to have a larger radius of curvature than the lower shear blade. When closing the blades for cutting, the lower shear blade elastically deforms in a direction for extending while the upper shear blade elastically deforms in a direction where it is bent in a manner tracking elastic deformation of the lower shear blade and is pushed against the lower shear blade while creating a contact point. This contact point is the location of cutting the object. Overall, the contact point moves from the bases to the tips. In the completely closed state, the cutting action ends. How the upper and lower shear blades are made to deform can be determined by the combination of the thickness, hardness, the bending deformability (groove cutting and other additional steps) employed.

INDUSTRIAL APPLICABILITY

According to the present invention, it is possible to provide scissors obtained by selecting materials sliding against each other, utilizing superelasticity to enable the shape of a blade to deform so that a shear blade slides against an opposite blade, and able to cut along an opposite blade, particularly medical use scissors in which smaller size is required, more particularly scissors able to be suitably used for neurosurgical procedures.

The invention claimed is:
1. Scissors comprising:
a pair of shanks with one ends forming an upper shear blade having a blade part and a lower shear blade having a blade part and with the other ends of the pair of shanks forming handles, the handles being opened and closed centered about a pivot where the shanks intersect and causing the upper shear blade and the lower shear blade to open and close,
at least one of the upper shear blade and lower shear blade being formed by a β-type titanium alloy, which is a nonmagnetic material, having an elastic deformation ability of 1% to 7% a tip side of the upper shear blade and the lower shear blade being curved upward in a vertical direction to a sliding surface of the shear blades; and
screws for loosely fastening the pivot with a degree of freedom so that the screws do not interfere with sliding of the blades when cutting an object, wherein
the blade part of the upper or lower shear blade is configured to cut while deforming so that a cutting edge part of the upper or lower shear blade slides against a curved surface of a cutting edge part of the other upper or lower shear blade, and wherein
the blade part of the upper shear blade or the lower shear blade is configured to move to create a single point of a cut part along the blade part of the other shear blade.

2. The scissors according to claim 1 wherein the upper shear blade is formed by an alloy having an elastic deformation ability of 0.2% or more.

3. The scissors according to claim 1 wherein a radius of curvature of the curve is in the range of 10 to 150 mm.

4. The scissors according to claim 3 wherein the radius of curvature is in the range of 20 to 100 mm.

5. The scissors according to claim 1 wherein a head of the screws fastening the pivot are enlarged to broadly form surfaces sliding with the outer sides of blade parts of the scissors and the blade parts are configured to move along the surfaces so that the shear blades constantly slide against each other.

6. The scissors according to claim 1 which utilize a superelasticity of the blades to cause the shear blades slide against each other when changing rates of curvature of the upper shear blade and the lower shear blade.

7. The scissors according to claim 1 for one or more of neurosurgical procedures, cardiovascular surgery procedures, plastic surgery procedures, and otorhinolaryngologic surgical procedures.

8. The scissors according to claim 1, wherein the β-type titanium alloy has a composition of Ti-23Nb-2Zr-0.7Ta—O (mol %), Ti-12Ta-9Nb-3V-6Zr—O (mol %), or Ti-36Nb-2Ta-3Zr—O (mol %).

* * * * *